(12) United States Patent
Ahmad et al.

(10) Patent No.: US 6,800,749 B1
(45) Date of Patent: Oct. 5, 2004

(54) G-PROTEIN COUPLED RECEPTOR

(75) Inventors: Sultan Ahmad, Quebec (CA); Jack Cao, Quebec (CA); Dajan O'Donnell, Quebec (CA); Philippe Walker, Quebec (CA)

(73) Assignee: AstraZeneca Canada Inc., Mississauga (CA)

( * ) Notice: Subject to any disclaimer, the term of this patent is extended or adjusted under 35 U.S.C. 154(b) by 0 days.

(21) Appl. No.: 09/341,016

(22) PCT Filed: Apr. 15, 1999

(86) PCT No.: PCT/SE99/00598

§ 371 (c)(1),
(2), (4) Date: Jul. 1, 1999

(87) PCT Pub. No.: WO99/55732

PCT Pub. Date: Nov. 4, 1999

(30) Foreign Application Priority Data

Apr. 24, 1998 (SE) .............................................. 9801455

(51) Int. Cl.[7] .............................................. C12N 15/12
(52) U.S. Cl. .................. 536/23.5; 435/69.1; 435/252.3; 435/320.1
(58) Field of Search ............................ 435/69.1, 252.3, 435/320.1; 536/23.5; 530/300

(56) References Cited

FOREIGN PATENT DOCUMENTS

WO    WO 94/29447    12/1994    ............ C12N/15/12

OTHER PUBLICATIONS

Fluhmann et al. A Human Orphan Calcitonin Receptor–Like Structure Jan. 5, 1995. Biochem. Biophys. Res. Comm. 206(1):341–347.*
Ross et al. RTA, a Candidate G proptein–coupled Receptor: Cloning, Sequencing, and Tissue Distribution. Apr. 1990, Biochemistry 87:3052–3056.*
Hosoya et al. Identification and Functional Characterization of a Novel Subtype of Neuromedin U Receptor. Sep. 22, 2000. J. Biol. Chem. 275(38):29528–29532.*
Zhou et al. Molecular Cloning and Characterization of an Adenosine Receptor: The A3 Adenosine Receptor. Aug. 1999, P.N.A.S. 89:7432–7436.*
Gantz et al. Cloning and Chromosomal Localization of a Gene (GPR18) Encoding a Novel Seven Transmembrane Receptor Highly Expressed in Spleen and Testes. Jun. 15, 1997. Genomics 42(3):462–466.*
Eva et al. Molecular Cloning of a Novel G protein–coupled Receptor that may belong to the Neuropeptide Receptor Family. Oct. 1990, FEBS Letters 271(1,2):81–84.*
Hillier, et al., "The WashU–Merck EST Project", Databus GenBank/DDBJ abstract, accession No. N45474.
Tyler, et al., "Evidence for Additional Neurotesin Receptor Subtypes: Neurotensin Analogs that Distinguish Between Neurotensin–Mediated Hypothermia and Antinociception," *Brain Res.* 792:246–252 (1998).
International Search Report for PCT/SE99/00598.
McKee, et al. "Cloning and Characterization of Two Human G Protein–Coupled Receptor Genes (GPR38 and GPR39) Related to the Growth Hormone Secretagogue and Neurotensin Receptors," *Genomics* 46:426–434 (1997).

* cited by examiner

*Primary Examiner*—John Ulm
(74) *Attorney, Agent, or Firm*—Michael A. Sanzo; Fitch, Even, Tabin & Flannery

(57) ABSTRACT

The present invention is directed to a novel neurotensin-like receptor expressed in the central nervous system of humans. The invention encompasses the receptor protein as well as nucleic acids encoding the protein. In addition, the invention is directed to methods and compositions which utilize the receptor.

12 Claims, 1 Drawing Sheet

```
TTTTTTTCCTGGCTCAGCTTGAAACAGAGCCTCGTACCAGGGGAGGCTCAGGCCTTGGATTTTAATGTC
AGGGATGGAAAAACTTCAGAATGCTTCCTGGATCTACCAGCAGAAACTAGAAGATCCATTCCAGAAAC
ACCTGAACAGCACCGAGGAGTATCTGGCCTTCCTCTGCGGACCTCGGCGCAGCCACTTCTTCCTCCCCG
TGTCTGTGGTGTATGTGCCAATTTTTGTGGTGGGGGTCATTGGCAATGTCCTGGTGTGCCTGGTGATTCT
GCAGCACCAGGCTATGAAGACGCCCACCAACTACTACCTCTTCAGCCTGGCGGTCTCTGACCTCCTGGT
CCTGCTCCTTGGAATGCCCCTGGAGGTCTATGAGATGTGGCGCAACTACCCTTTCTTGTTCGGGCCCGT
GGGCTGCTACTTCAAGACGGCCCTCTTTGAGACCGTGTGCTTCGCCTCCATCCTCAGCATCACCACCGT
CAGCGTGGAGCGCTACGTGGCCATCCTACACCCGTTCCGCGCCAAACTGCAGAGCACCCGGCGCCGGGCC
CTCAGGATCCTCGGCATCGTCTGGGGCTTCTCCGTGCTCTTCTCCCTGCCCAACACCAGCATCCATGGC
ATCAAGTTCCACTACTTCCCCAATGGGTCCCTGGTCCCAGGTTCGGCCACCTGTACGGTCATCAAGCCC
ATGTGGATCTACAATTTCATCATCCAGGTCACCTCCTTCCTATTCTACCTCCTCCCCATGACTGTCATCA
GTGTCCTCTACTACCTCATGGCACTCAGACTAAAGAAGGACAAATCTCTTGAGGCAGATGAAGGGAAT
GCAAATATTCAAAGACCCTGCAGAAAATCAGTCAACAAGATGCTGCTTGTCTTGGTCTTAGTGTTTGCT
ATCTGTTGGGCCCCGTTCCACATTGACCGACTCTTCTTCAGCTTTGTGGAGGAGTGGACTGAATCCCTG
GCTGCTGTGTTCAACCTCGTCCATGTGGTGTCAGGTGTCTTATTCTACCTGAGCTCAGCTGTCAACCCCA
TTATCTATAACCTACTGTCTCGCCGCTTCCAGGCAGCATTCCAGAATGTGATCTCTTCTTTCCACAAACA
GTGGCACTCCCAGCATGACCCACAGTTGCCACCTGCCCAGCGGAACATCTTCCTGACAGAATGCCACTT
TGTGGAGCTGACCGAAGATATAGGTCCCCAATTCCCATGTCAGTCATCCGTGCACAACTCTCACCTCCC
AACAGCCCTCTCTAGTGAACAGATGTCAAGAACAAACTATCAAAGCTTCCACTTTAACAAAACCTGAA
TTCTTTCAGAGCTGACTCTCCTCTATGCCTCAAAACTTCACAGAGGA
```

FIG.1

```
MSGMEKLQNASWIYQQKLEDPFQKHLNSTEEYLAFLCGPRRSHFFLPVSVVYVPIFVVGVIGNVLVCLVILQ
HQAMKIPINYYLFSLAVSDLLVLLLGMPLEVYEMWRNYPFLFGPVGCYFKTALFETVCFASILSITTVSVER
YVAILHPFRAKLQSTRRRALRILGIVWGFSVLFSLPNTSIHGIKFHYFPNGSLVPGSATCTVIKPMWIYNFIIQV
TSFLFYLLPMTVISVLYYLMALRLKKDKSLEADEGNANIQRPCRKSVNKMLLVLVLVFAICWAPFHIDRLFF
SFVEEWTESLAAVFNLVHVVSGVLYLSSAVNPIIYNLLSRRFQAAFQNVISSFHKQWHSQHDPQLPPAQRN
IFLTECHVELTEDIGPQFPCQSSVHNSHLPTALSSEQMSRTNYQSFHFNKT
```

FIG.2

G-PROTEIN COUPLED RECEPTOR

The present application represents U.S. national stage of international application PCT/SE99/00598 with an international filing date of Apr. 15, 1999. The international application was published in English under Article 21(2) of the PCT on November 4, 1999. It claims priority to Swedish application 9801455-8, filed on Apr. 24, 1988.

FIELD OF THE INVENTION

The present invention is in the general field of biological receptors and the various uses that can be made of such receptors. More specifically, the invention relates to nucleic acids encoding a novel neurotensin-like receptor (NLR) and to the receptor itself.

BACKGROUND OF THE INVENTION

G protein-coupled receptors (GPCRs) constitute a family of proteins sharing a common structural organization characterized by an extracellular N-terminal end, seven hydrophobic alpha helices putatively constituting transmembrane domains and an intracellular C-terminal domain. GPCRs bind a wide variety of ligands that trigger intracellular signals through the activation of transducing G proteins (Caron, et al., *Rec. Prog. Horm. Res.* 48:277–290 (1993); Freedman et al., Rec. Prog. Horm. Res. 51:319–353 (1996)).

More than 300 GPCRs have been cloned thus far and it is generally assumed that there exist well over 1000 such receptors. Mechanistically, approximately 50–60% of all clinically relevant drugs act by modulating the functions of various GPCRs (Cudermann, et al., *J. Mol. Med.* 73:51–63 (1995)). Of particular interest are receptors located in the central nervous system. G protein-coupled receptors located in this region are known to be involved in the transmission, modulation and sensation of pain. Thus, new G protein-coupled receptors found in the brain and spinal column may be used in assays for the identification of new agents for producing anesthesia and analgesia.

SUMMARY OF THE INVENTION

The present invention is based upon the discovery of a novel G protein-coupled receptor which is expressed in the central nervous system and has a structure distinct from all previously reported receptors. Since it appears to share a substantial homology with the human neurotensin receptor, it is referred to herein as the "neurotensin-like receptor."

In its first aspect, the invention is directed to a protein, except as existing in nature, comprising an amino acid sequence consisting functionally of SEQ ID NO:1. The term "consisting functionally of" refers to proteins in which the sequence of SEQ ID NO:1 has undergone additions, deletions or substitutions which do not substantially alter the functional characteristics of the receptor. The term is intended to encompass proteins having exactly the same amino acid sequence as that of SEQ ID NO:1, as well as proteins with sequence differences that are not substantial as evidenced by their retaining the basic, qualitative ligand binding and physiological properties of the neurotensin-like receptor. The term "except as existing in nature" refers to a compound that is either expressed by recombinant means or that is in a purified (preferably substantially purified) state.

The invention also encompasses a protein, except as existing in nature, having an amino acid sequence consisting essentially of the sequence of SEQ ID NO:1; antibodies that bind preferentially to such a protein (i.e., antibodies having at least a 100-fold greater affinity for NLR than any other protein); and antibodies made by a process involving the injection of a pharmaceutically acceptable preparation of NLR into an animal capable of antibody production.

In a preferred embodiment, monoclonal antibody to NLR is produced by administering, preferably by injection, NLR to a mouse and then fusing the mouse's spleen cells with myeloma cells.

The invention is also directed to a polynucleotide, except as existing in nature, encoding a protein comprising an amino acid sequence consisting functionally of SEQ ID NO:1. This aspect of the invention encompasses polynucleotides encoding proteins consisting essentially of the amino acid sequence of SEQ ID-NO:1, expression vectors comprising such polynucleotides, and host cells transformed with such vectors. Also included is the recombinant neurotensin-like receptor produced by host cells made in this manner.

Preferably, the polynucleotide encoding the neurotensin-like receptor has the nucleotide sequence shown in SEQ ID NO:2, and the vectors and host cells used for expression of the receptor also use this particular polynucleotide.

In another aspect, the present invention is directed to a method for assaying a test compound for its ability to bind to a human neurotensin-like receptor. The method is performed by incubating a source of NLR with a ligand known to bind to the receptor and with the test compound. The source of receptor should, preferably, express a large amount of NLR relative to other G protein-coupled receptors. Upon completion of incubation, the ability of the test compound to bind to NLR is determined by the extent to which ligand binding has been displaced. Preferably, the receptor present should have the sequence shown in SEQ ID NO:1. Although not essential, the binding assay can be accompanied by an assay to determine whether a second messenger pathway, e.g., the adenyl cyclase pathway, has become activated. This should help to determine whether a particular compound binding to NLR is acting as an agonist or antagonist.

An alternative method for determining if a test compound is an NLR agonist, a method that does not require any ligand, is to use a cell signaling assay, e.g., an assay measuring either intracellular adenyl cyclase activity or intracellular calcium concentration. The test compound should generally be incubated with cells expressing high amounts of NLR relative to other G protein-coupled receptors, typically a cell transfected with an expression vector encoding the NLR of SEQ ID NO:1. Test compounds that are agonists are identified by their causing a statistically significant change in the results obtained from the cell signaling assay when compared to control cells not exposed to test compound. The control cells may be either cells that have not been transfected or cells that have been mock transfected with a vector that does not produce active receptor. NLR-expressing cells exposed to test compounds that are agonists would typically be expected to show a significant increase in adenyl cyclase activity or in intracellular calcium concentration relative to control cells.

The invention also encompasses a method for determining if a test compound is an antagonist of NLR which relies upon the known constitutive activation of G protein-coupled receptors that occurs when such receptors are expressed in large amounts. This method requires that DNA encoding the receptor be incorporated into an expression vector so that it is operably linked to a promoter and that the vector then be used to transfect an appropriate host. In order to produce sufficient receptor to result in constitutive receptor activation (i.e., activation in the absence of natural ligand), expression systems capable of copious protein production are preferred, e.g., the NLR DNA may be operably linked to a CMV promoter and expressed in COS or HEK293 cells. After transfection, cells with activated receptors are selected based upon their showing increased activity in a cell signaling assay relative to comparable cells that have either not been transfected or that have been transfected with a vector that is incapable of expressing functional NLR. Typically, cells will be selected either because they show a statistically significant change in intracellular adenyl cyclase activity or in intracellular calcium concentration. The selected cells are contacted with the test compound and the cell signaling assay is repeated to determine if this results in a decrease in activity relative to selected cells that have not been contacted with the test compound. For example, a statistically significant decrease in either adenyl cyclase activity or calcium concentration relative to control cells would indicate that the test compound is an antagonist of NLR. Preferably the NLR used in assays has the sequence of SEQ ID NO:1.

Assays for compounds interacting with NLR may be performed by incubating a source containing the receptor (e.g., a stably transformed cell) with a ligand specific for NLR both in the presence and absence of test compound and measuring the modulation of intracellular calcium concentration. A significant increase or decrease in ligand-stimulated calcium signaling in response to test compound is indicative of an interaction occurring at the neurotensin-like receptor. The preferred receptor is that having the amino acid sequence of SEQ ID NO:1.

In another aspect, the present invention is directed to a method for assaying a test compound for its ability to alter the expression of NLR. This method is performed by growing cells expressing NLR in the presence of the test compound. Cells are then collected and the expression of NLR is compared with expression in control cells grown under essentially identical conditions but in the absence of test compound. The preferred receptor is one having the amino acid sequence of SEQ ID NO:1. A preferred test compound is an oligonucleotide at least 15 nucleotides in length comprising a sequence complementary to the sequence of the NLR mRNA used in the assay.

BRIEF DESCRIPTION OF THE DRAWINGS

FIG. 1. FIG. 1 contains the complete nucleotide sequence of a clone (SEQ ID NO:2) constructed by the methods described in the Examples section. The clone was deposited with the International Depository Authority Deutsche Sammlung Von Mikroorganismen Und Zellkulturen GmbH (DSMZ) at the address Mascheroder Weg 1B, D-38124 Braunschweig, Germany. The deposit (plasmid pcDNA 3-10-29-FL) was made on Apr. 9, 1988 and was given the accession number DSM 12101. The amino acid sequence of human NLR begins at nucleotide 65 and ends with the termination codon that begins at nucleotide 1310.

FIG. 2. FIG. 2 shows the deduced amino acid sequence of human NLR (SEQ ID NO:1). The polynucleotide of FIG. 1 codes for a protein 415 amino acids in length.

DEFINITIONS

The description that follows uses a number of terms that refer to recombinant DNA technology. In order to provide a clear and consistent understanding of the specification and claims, including the scope to be given such terms, the following definitions are provided.

Cloning vector: A plasmid or phage DNA or other DNA sequence which is able to replicate autonomously in a host cell and which is characterized by one or a small number of restriction endonuclease recognition sites. A foreign DNA fragment may be spliced into the vector at these sites in order to bring about the replication and cloning of the fragment. The vector may contain a marker suitable for use in the identification of transformed cells. For example, markers may provide tetracycline resistance or ampicillin resistance.

Expression vector: A vector similar to a cloning vector but which is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

Substantially pure: As used herein, "substantially pure" means that the desired product is essentially free from contaminating cellular components. A "substantially pure" protein or nucleic acid will typically comprise at least 85% of a sample, with greater percentages being preferred. Contaminants may include proteins, carbohydrates or lipids. One method for determining the purity of a protein or nucleic acid is by electrophoresing a preparation in a matrix such as polyacrylamide or agarose. Purity is evidenced by the appearance of a single band after staining. Other methods for assessing purity include chromatography and analytical centrifugation.

Recombinant protein: A recombinant protein or recombinant receptor is a non-endogenous protein produced by the introduction of an expression vector into host cells.

Host: Any prokaryotic or eukaryotic cell that is the recipient of a replicable expression vector or cloning vector is the "host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g. Sambrook et al., Molecular Cloning: A Laboratory Manual, 2nd ed. Cold Spring Harbor (1989)).

Promoter: A DNA sequence typically found in the 5' region of a gene, located proximal to the start codon. Transcription is initiated at the promoter. If the promoter is of the inducible type, then the rate of transcription increases in response to an inducing agent.

Complementary Nucleotide Sequence: A complementary nucleotide sequence, as used herein, refers to the sequence that would arise by normal base pairing. For example, the nucleotide sequence 5'-AGAC-3' would have the complementary sequence 5'-GTCT-3'.

Expression: Expression is the process by which a polypeptide is produced from DNA. The process involves the transcription of the gene into mRNA and the translation of this mRNA into a polypeptide.

DETAILED DESCRIPTION OF THE INVENTION

The present invention is directed to a neurotensin-like receptor protein, genetic sequences coding for the protein, a method for assaying compounds for binding to neurotensin-like receptors and a method for assaying compounds for their ability to alter receptor expression.

The receptor and its nucleic acid are defined by the structures shown in FIGS. 1 and 2 and by SEQ ID NOs:1 and 2. However, the invention encompasses not only sequences identical to those shown in the figures and sequence listing, but also sequences that are essentially the same and sequences that are otherwise substantially the same and which result in a receptor retaining the basic binding characteristics of NLR. For example, it is well known that techniques such as site-directed mutagenesis may be used to introduce variations into a protein's structure. Variations in the neurotensin-like receptor introduced by this or some similar method are encompassed by the invention provided that the resulting receptor retains the basic qualitative binding and physiological characteristics of unaltered NLR. Thus, the invention relates to proteins comprising amino acid sequences consisting functionally of SEQ ID NO:1.

I. Nucleic Acid Sequences Coding for NLR

DNA sequences coding for the human neurotensin-like receptor are expressed in the central nervous system, placenta and skeletal muscle and any of these may serve as a source for the isolation of nucleic acids coding for the receptor. In addition, cells and cell lines that express human NLR may be used. These may either be cultured cells that have not undergone transformation or cell lines specifically engineered to express recombinant NLR. In all cases, poly A$^+$mRNA is isolated from the tissue or cells, reverse transcribed and cloned. The cDNA library thus formed may then be screened using probes derived from SEQ ID NO:2. Probes should typically be at least 14 bases in length and should, preferably, not be obtained from the regions of the DNA corresponding to the highly conserved transmembrane domains of NLR.

Alternatively, the human neurotensin-like receptor can be obtained from recombinant cells containing the full length NLR sequence or from cDNA libraries by performing PCR amplifications with primers located at either end of the NLR gene. These primers can be selected from the sequences shown in SEQ ID NO:2. The Examples section describes a procedure by which PCR amplifications were used to obtain the neurotensin-like receptor from fetal spinal cord cDNA.

II. Antibodies to NLR

The present invention also is directed to antibodies that bind specifically to the human neurotensin-like receptor and to a process for producing such antibodies. Antibodies that "bind specifically" are defined as those that have at least a one hundred fold greater affinity for NLR than for any other protein. The process for producing such antibodies may involve either injecting the NLR protein itself into an appropriate animal or, alternatively, injecting short peptides made to correspond to different regions of the receptor. The peptides should be at least five amino acids in length and should be selected from regions believed to be unique to NLR.

Thus, highly conserved transmembrane regions should generally be avoided in selecting peptides for the generation of antibodies. Methods for making and detecting antibodies are well known to those of skill in the art as evidenced by standard reference works such as: Harlow et al., *Antibodies, A Laboratory Manual*, Cold Spring Harbor Laboratory, N. Y. (1988)); Klein, Immunology: *The Science of Self-Nonself Discrimination* (1982); Kennett, et al., *Monoclonal Antibodies and Hybridomas: A New Dimension in Biological Analyses* (1980); and Campbell, "*Monoclonal Antibody Technology,*" in *Laboratory Techniques in Biochemistry and Molecular Biology*, (1984)).

"Antibody," as used herein, is meant to include intact molecules as well as fragments which retain their ability to bind to antigen (e.g., Fab and F(ab')$_2$ fragments). These fragments are typically produced by proteolytically cleaving intact antibodies using enzymes such as papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in: *Monoclonal Antibodies and T-Cell Hybridomas*, Elsevier, M. Y., pp. 563–681 (1981)). In general, this technology involves immunizing an animal, usually a mouse, with either intact NLR or a fragment derived from NLR. The splenocytes of the immunized animals are extracted and fused with suitable myeloma cells, e.g., SP$_2$O cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding to NLR.

The antibodies, or fragments of antibodies, of the present invention may be used to detect the presence of NLR using any of a variety of immunoassays. For example, the antibodies may be used in radioimmunoassays or in immunometric assays, also known as "two-site" or "sandwich" assays (see Chard, T., "*An Introduction to Radioimmune Assay and Related Techniques,*" in *Laboratory Techniques in Biochemistry and Molecular Biology*, North Holland Publishing Co., N.Y (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see e.g., *Radioimmune Assay Method*, Kirkham et al., ed., pp. 199–206, E & S. Livingstone, Edinburgh (1970)). Many variations of these types of assays are known in the art and may be employed for the detection of NLR.

Antibodies to human NLR may also be used in the purification of either intact receptor or fragments of the receptor (see generally, Dean et al., *Affinity Chromatography, A Practical Approach*, IRL Press (1986)). Typically, antibody is immobilized on a chromatographic matrix such as Sepharose 4B. The matrix is then packed into a column and the preparation containing NLR is passed through under conditions that promote binding, e.g., under conditions of low salt. The column is then washed and bound NLR is eluted using a buffer that promotes dissociation from antibody, e.g., buffer having an altered pH or salt concentration. The eluted NLR may be transferred into a buffer of choice, e.g., by dialysis, and either stored or used directly.

III. Radioligand Assay for Receptor Binding

One of the main uses for NLR nucleic acids and recombinant proteins is in assays designed to identify agents capable of binding to the receptor. Such agents may either be agonists, mimicking the normal effects of receptor binding, or antagonists, inhibiting the normal effects of receptor binding. Of particular interest is the identification of agents which bind to the neurotensin-like receptor and modulate intracellular signalling, such as adenyl cyclase activity or intracellular calcium. These agents have potential therapeutic application as either analgesics or anesthetics.

In radioligand binding assays, a source of NLR is incubated together with a ligand known to bind to the receptor and with the compound being tested for binding activity. The preferred source of NLR is cells, preferably mammalian cells, transformed to recombinantly express the receptor. The cells selected should not express a substantial amount of any other G protein-coupled receptor that might bind to ligand and distort results. This can easily be determined by performing binding assays on cells derived from the same tissue or cell line as those recombinantly expressing NLR but which have not undergone transformation.

The assay may be performed either with intact cells or with membranes prepared from the cells (see e.g., Wang, et al., *Proc. Natl. Acad. Sci. U.S.A.* 90:10230–10234 (1993)). The membranes, or cells, are incubated with a ligand specific for the NLR receptor and with a preparation of the compound being tested. After binding is complete, receptor is separated from the solution containing ligand and test compound, e.g., by filtration, and the amount of binding that has occurred is determined. Preferably, the ligand used is detectably labeled with a radioisotope such as $^{125}$I. However, if desired, fluorescent or chemiluminescent labels can be used instead. Among the most commonly used fluorescent labeling compounds are fluorescein isothiocynate, rhodamine, phycoerythrin, phycocyanin, allophycocyanin, o-phthaldehyde and fluorescamine. Useful chemiluminescent compounds include luminol, isoluminol, theromatic acridinium ester, imidazole, acridinium salt, and oxalate ester. Any of these agents can be used to produce a ligand suitable for use in the assay.

Nonspecific binding may be determined by carrying out the binding reaction in the presence of a large excess of unlabeled ligand. For example, labeled ligand may be incubated with receptor and test compound in the presence of a thousandfold excess of unlabeled ligand.

Nonspecific binding should be subtracted from total binding, i.e. binding in the absence of unlabeled ligand, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with the neurotensin-like receptor when, in fact, binding is being inhibited by some other mechanism. For example, the compound being tested should be in a buffer which does not itself substantially inhibit the binding of ligand to NLR and should, preferably, be tested at several different concentrations. Preparations of test compound should also be examined for proteolytic activity and it is desirable that antiproteases be included in assays. Finally, it is highly desirable that compounds identified as displacing the binding of ligand to NLR receptor be reexamined in a concentration range sufficient to perform a Scatchard analysis of the results. This type of analysis is well known in the art and can be used for determining the affinity of a test compounds for receptor (see e.g., Ausubel, et al., *Current Protocols in Molecular Biology*, 11.2.1–11.2.19 (1993); *Laboratory Techniques in Biochemistry and Molecular Biology*, Work, et al., ed., N.Y. (1978) etc.). Computer programs may be used to help in the analysis of results (see e.g. Munson, P., *Methods Enzymol.* 92:543–577 (1983); McPherson, G. A., Kinetic, EBDA Ligand, Lowry-*A Collection of Radioligand Binding Analysis Programs*, Elsevier-Biosoft, U.K. (1985)).

The activation of receptor by the binding of ligand may be monitored using a number of different assays. For example, adenyl cyclase assays may be performed by growing cells in wells of a microtiter plate and then incubating the wells in the presence or absence of test compound. cAMP may then be extracted in ethanol, lyophilized and resuspended in assay buffer. Assay of cAMP thus recovered may be carried out using any method for determining cAMP concentration, e.g. the Biotrack cAMP Enzyme-immunoassay System (Amersham) or the Cyclic AMP [$^3$H] Assay System (Amersham). Typically, adenyl cyclase assays will be performed separately from binding assays, but it may also be possible to perform binding and adenyl cyclase assays on a single preparation of cells. Other "cell signaling assays" that can be used to monitor receptor activity are described below.

IV. Identification of NLR Agonists and Antagonists Using Cell Signaling Assays

Neurotensin-like receptors may also be used to screen for drug candidates using cell signaling assays. To identify NLR agonists, the DNA encoding a receptor is incorporated into an expression vector and then transfected into an appropriate host. The transformed cells are then contacted with a series of test compounds and the effect of each is monitored. Among the assays that can be used are assays measuring cAMP production (see discussion above), assays measuring the activation of reporter gene activity, assays measuring the modulation of the binding of ligand, e.g., GTP-gamma-S, or assays measuring changes in intracellular calcium concentration.

Cell signaling assays may also be used to identify NLR antagonists. G protein-coupled receptors can be put into their active state even in the absence of their cognate ligand by expressing them at very high concentration in a heterologous system. For example, receptor may be overexpressed using the baculovirus infection of insect Sf9 cells or the NLR gene may be operably linked to a CMV promoter and expressed in COS or HEK293 cells. In this activated constitutive state, antagonists of the receptor can be identified in the absence of ligand by measuring the ability of a test compound to inhibit constitutive cell signaling activity. Appropriate assays for this are, again, cAMP assays, reporter gene activation assays or assays measuring the binding of GTP-gamma-S.

One preferred cell signaling assay is based upon cells stably transfected with NLRs showing a change in intracellular calcium levels in response to incubation in the presence of ligand. Thus, a procedure can be used to identify NLR agonists or antagonists that is similar to the radioreceptor assays discussed above except that calcium concentration is measured instead of bound radioactivity. The concentration of calcium in the presence of test compound and ligand is compared with that in the presence of ligand alone to determine whether the test compound is interacting at the neurotensin-like receptor. A statistically significant increase in intracellular calcium in response to test compound indicates that the test compound is acting as an agonist whereas a statistically significant decrease in intracellular calcium indicates that it is acting as an antagonist.

Assays may also be performed that measure the activation of a reporter gene. For example, cells expressing recombinant NLR receptor may be transfected with a reporter gene (e.g., a chloramphenicol acetyltransferase or luciferase gene) operably linked to an adenyl cyclase or diacylglycerol response element. The cells are then incubated with test compounds and the expression of the reporter gene is compared to expression in control cells that do not express recombinant NLR but that are essentially identical in other respects. A statistically significant change in reporter gene expression in the NLR-expressing cells is indicative of a test compound that interacts with the NLR receptor.

V. Assay for Ability to Modulate NLR Expression

One way to either increase or decrease the biological effects of NLR is to alter the extent to which the receptor is expressed in cells. Therefore, assays for the identification of compounds that either inhibit or enhance expression are of considerable interest. These assays are carried out by growing cells expressing NLR in the presence of a test compound and then comparing receptor expression in these cells with expression in cells grown under essentially identical conditions but in the absence of test compound. As in the binding assays discussed above, it is desirable that the cells used be substantially free of competing G protein-coupled receptors. One way to measure receptor expression is to fuse the NLR sequence to a sequence encoding a peptide or protein that can be readily quantitated. For example, the NLR sequence may be ligated to a sequence encoding hemagglutinin and used to stably transfect cells. After incubation with test compound, the haemaglutinin/ receptor complex can be immuno-precipitated and Western blotted with anti-haemaglutinin antibody. Alternatively, Scatchard analysis of binding assays may be performed with labeled ligand to determine receptor number. The binding assays may be carried out as discussed above and will preferably utilize cells that have been engineered to recombinantly express NLR.

A preferred group of test compounds for inclusion in the NLR expression assay consists of oligonucleotides complementary to various segments of the NLR nucleic acid sequence as shown in SEQ ID NO:2. These oligonucleotides should be at least 15 bases in length and should be derived from non-conserved regions of the receptor nucleic acid sequence.

Oligonucleotides which are found to reduce receptor expression may be derivatized or conjugated in order to increase their effectiveness. For example, nucleoside phosphorothioates may be substituted for their natural counterparts (see Cohen, J., *Oligodeoxynucleotides, Antisense Inhibitors of Gene Expression*, CRC Press (1989)). The oligonucleotides may be delivered to a patient in vivo for the purpose of inhibiting DRR expression. When this is done, it is preferred that the oligonucleotide be administered in a form that enhances its uptake by cells. For example, the oligonucleotide may be delivered by means of a liposome or conjugated to a peptide that is ingested by cells (see e.g., U.S. Pat. Nos. 4,897,355 and 4,394,448; see also non-U.S. patent documents WO 8903849 and EP 0263740). Other methods for enhancing the efficiency of oligonucleotide delivery are well known in the art and are also compatible with the present invention.

Having now described the invention, the same will be more readily understood through reference to the following Examples which are provided by way of illustration and which are not intended to limit the scope of the invention.

EXAMPLES

Example 1

Cloning of Human NLR

A pair of degenerate oligonucleotides were designed based on the conserved peptide sequences among the various members of opioid and somatostatin receptor family. The primer sequences are as follows:

5'-AARMTSAARACIGCYACIAA-3' (SEQ ID NO:3) forward primer 1I-U; and

5'-AYRGCGAYRTAICKRTCIAC-3' (SEQ ID NO:4) reverse primer 2I-L.

The polymerase chain reaction mixture (total volume 100 4 µl) contained ~250 ng of the human genomic DNA (NOVAGEN), 1×PCR buffer (50 mM KCl, 1.5 mM MgCl$_2$, 10 mM Tris-HCI (pH 8.9), Pharmacia), 200 µM dNTPs (Pharmacia), 200 pmol each of the above primers, and 5U Taq polymerase (Pharmacia). Amplifications were carried out on a RoboCycler Gradient 40 (Stratagene). Template was denatured at 95° C. for one minute, followed by 35 cycles consisting of the denaturation, annealing and extension steps each for one min at 95° C., 42° C. and 72° C., respectively. The resulting products were resolved on an 1% agarose gel. An expected major band around 220 bp was excised and purified with the Sephaglas BandPrep Kit (Pharmacia) and cloned into pGEM-T (Promega). Plasmids were prepared with the alkaline lysis protocol and screened with the dideoxy termination sequencing method of Sanger et al. The majority of the cloned PCR products were found to be the human delta opioid receptor which was removed by bacterial colony hybridization. Among the other known human opioid (kappa and mu) receptors and hORL1 (Orphanin FQ or nociceptin receptor) was a novel putative G-protein coupled receptor, termed 10-29.

PCR was used to first determine which human tissue cDNA library to screen with a pair of primers designed based upon the original PCR fragment (see above): The sequences of the oligonucleotides were:

5'-TGGTCCTGCTCCTTGGAATG (SEQ ID NO:5) 29-1, forward primer; and

5'-GCGAAGCACACGGTCTCAAA (SEQ ID NO:6) 29-2, reverse primer.

The PCR mixture (total volume 30 µl) contained 1 µl of QUICK-Screen Human cDNA Library Panel (CLONTECH, Cat# k1003-1), 1×PCR buffer (Pharmacia), 200 µM dNTPs (Pharmacia), 25 pmol of each primer and 1 U of Taq polymerase (Pharmacia). The initial denaturation of the templates for one min at 95° C. was followed by 45 cycles of denaturation, annealing and extension each for one min at 95° C., 55° C. and 72° C., respectively. The brain, placenta, skeletal muscle and, at much lower level, kidney libraries were found to contain positive clones (data not shown). A human brain λgt11 cDNA library (CLONTECH, Cat#HL3002b) was chosen to screen for the gene with the original 220 bp PCR fragment as probe, labeled by the random priming method (Ready-To-Go DNA labeling Beads (-dCTP), Pharmacia). Prehybridization and hybridization were carried out at 62° C. in 2X SSC, 5X Denhardt's solution, 0.5% SDS and 100µg/ml Herring sperm DNA. Probe concentration was about 0.5×106 cpm/ml. One positive clone was identified. The insert of this clone was excised, subcloned into pBlueScript, and named pBS 10-29.

The clone pBS 10-29 contains the complete N-terminus for the putative receptor; but the coding region is interrupted by stop codons at the end of transmembrane region 5 (TM5) and the homology to hNTR1 is also lost beyond this region. Apparently, in this cDNA, the introns are not completely spliced out. A human P1 genomic DNA clone was obtained using primers 29-1(forward primer, see above) and 29-B:

5'-GGGGAAGTAGTGGAACTTGATGC-3', (SEQ ID NO:7) reverse primer.

This P1 clone was digested with Stu-I restriction endonuclease and the digest was electrophoresed, Southern blotted and screened with the 10-29 probe described earlier. An 8.5 kb StuI fragment of the P1 clone was identified that yielded a strong signal upon hybridization. This fragment was subcloned into pBlueScript, named pBS 10–29–8k and completely sequenced. It was found to include 12 bp upstream of the start codon and the coding region up to the TM-5 region, but it did not contain sequence information for the C-terminus of the receptor.

Another 11 kb Kpn 1 fragment, overlapping with the 8 kb fragment at about 1.3 kb from the 3' end of the latter, was also subcloned into pBlueScript (pBS 10-29-11k). After amplification in bacteria, the Kpn1 fragment was isolated in large quantity and completely digested with Sau3AI. The resulting fragments were randomly cloned into pBluescript and sequenced. Two clones, 8 and 74, were found to be identical and to contain a stretch encoding the TM7 region. Primers were designed around this region allowing for the determination of sequences further upstream, the complete C terminal and the 3' untranslated region. The results suggested that there is another intron upstream of TM7 since a recognizable TM6 was not found at the expected position relative to the TM7 region.

Using the primer 3'-270r (5'-TCCTCTGTGAAGTTTTGAGGC-3' (SEQ ID NO:8)) corresponding to a sequence in the 3' untranslated region, it was possible to clone the complete C-terminus of the 10-29 gene by nested PCR, using two 10-29 specific, nested forward primers, 29-1, see above, and 29-f3':5'-ATCGTCTGGGGCTTCTCCG-3' (SEQ ID NO:9). One 1 μl of cDNA prepared from human fetal spinal cord with DRGs attached was selected as a template for the first round of PCR; the nested PCR amplifications were performed using the previous PCR products (1 μl ) as templates. PCR conditions were the same as described above, except for the annealing temperature (50° C.) and the number cycles (35). An 857 bp fragment was amplified, cloned into pGEM-T (easy) (Promega) and sequenced. This clone was termed 29-CT (for C-terminus) and was found to share 222 bp with pBS 10-29 up to the position where the first intron starts. The rest of the sequence encodes the remaining part of the 10-29 gene. Combining both sequences forms the whole coding region of the receptor, totaling 1245 bp and having a deduced receptor protein of 415 amino acids.

The complete nucleotide sequence of the composite cDNA clone is illustrated in FIG. 1. The open reading frame comprising of 1245 nucleotides codes for a protein of 415 amino acids (FIG. 2) with a predicted molecular mass of ~43.6 kdaltons. The protein sequence contains all the characteristic features of GPCRs-seven hydrophobic helices likely to represent transmembrane domains, an amino terminus and a carboxy terminus domain. There is a potential glycosylation site at the N-terminal extracellular domain (position 9) and a conserved NPXXY sequence at position 323–327.

The nucleotide sequence and primary predicted amino acid sequence of receptor 10-29 most closely resemble the sequences of neurotensin receptors NTR-1 and NTR-2. A sequence alignment of receptor 10-29 with the known neurotensin receptors reveals that it is about 32% identical to the human and rat NTR-1 and NTR-2. Among the transmembrane domains, the highest degree of homology is seen in the TM-2 region (61 %) and the lowest in TM-4 region (20%). The similarity in the amino acids between NTR-1, NTR-2 and receptor 10-29 is particularly high (>55%), suggesting that neurotensin may serve as the endogenous ligand for the receptor 10-29 Thus, receptor 10-29 may be a novel subtype of neurotensin receptor.

Example 2

In Situ Hybridization Experiments

Preparation of tissue: Frozen adult and fetal human spinal cord and dorsal root ganglia were obtained from the Brain and Tissue Bank for Developmental Disorders, University of Maryland at Baltimore, according to the strictest ethical guidelines. Adult male Sprague-Dawley rats (~250 gm; Charles River, St-Constant, Quebec) were sacrificed by decapitation. Brain and spinal cord with DRGs still attached were promptly removed, snap-frozen in isopentane at −40° C. for 20 s and stored at −80° C. Frozen tissue was sectioned at 16 μm in a Microm HM 500 M cryostat (Germany) and thaw-mounted onto ProbeOn Plus slides (Fisher Scientific, Montreal, Quebec). Sections were stored at −80° C. prior to in situ hybridization.

Riboprobe synthesis: The plasmid pCDNA3-10-29 (containing a 506 bp fragment) was linearized using either XbaI or HindIII restriction enzymes which cut in the polylinker on either side of the inserted cDNA. Antisense and sense 10-29 riboprobes were transcribed in vitro using either T7 or SP6 RNA polymerases (Pharmacia Biotech), respectively in the presence of [$^{35}$S]UTP (~800 Ci/mmol; Amersham, Oakville, Ontario). Following transcription, the DNA template was digested with DNAse I (Pharmacia). Riboprobes were subsequently purified on ProbeQuant G-50 micro columns (Pharmacia Biotech, USA) according to manufacturer's specifications. Quality of labeled riboprobes was verified by polyacrylamide-urea gel electrophoresis.

In situ Hybridization: Sections were postfixed in 4% paraformaldehyde (BDH, Poole, England) in 0.1 M phosphate buffer (pH 7.4) for 10 minutes at room temperature (RT) and rinsed in 3 changes of 2× standard sodium citrate buffer (SSC; 0.15 M NaCl. 0.015 M sodium citrate. pH 7.0). Sections were then equilibrated in 0.1 M triethanolamine, treated with 0.25% acetic anhydride in triethanolamine, rinsed in 2×SSC and dehydrated in an ethanol series (50–100%). Hybridization was performed in a buffer containing 75% formamide (Sigma, St-Louis, Mo.), 600 mM NaCl, 10 mM Tris (pH 7.5),1 mM EDTA,1× Denhardt's solution (Sigma), 50 mg/ml denatured salmon sperm DNA (Sigma), 50 mg/ml yeast tRNA (Sigma), 10% dextran sulfate (Sigma), 20 mM dithiothreitol and [$^{35}$S]UTP-labeled cRNA probes (10×106 cpm/ml) at 55° C. for 18 hours in humidified chambers. Following hybridization, slides were rinsed in 2×SSC at room temperature, treated with 20 mg/ml RNase IA (Pharmacia) in RNase buffer (10 mM Tris, 500 mM NaCl,1 mM EDTA, pH 7.5) for 45 min at room temperature and washed to a final stringency of 01×SSC at 65° C. Sections were then dehydrated and exposed to Kodak Biomax MR film for 17–21 days and/or dipped in Kodak NTB2 emulsion diluted 1:1 with distilled water and exposed for 6 weeks at 4° C. prior to development and counterstaining with cresyl violet acetate (Sigma).

Results: The expression pattern of Clone 10-29 in human adult spinal cord is quite unique as seen both at the level of film autoradiograms and by high resolution emulsion autoradiography. At all segmental levels examined (cervical, thoracic and lumbar), only a few neurons specifically expressed 10-29 mRNA and these cells were restricted to 3 functionally distinct regions of the spinal gray matter, namely the substantia gelatinosa, Clarke's nucleus and the ventral horn. Within the substantia gelatinosa, a modest proportion (<10%) of small, highly labeled neurons were scattered throughout the field. Hybridization signal in Clarke's nucleus was dramatic with a few individual cells expressing very high levels of 10-29 mRNA. Microscopic analysis revealed that the signal was exclusively associated with most, but not all, large neurons of Clarke's nucleus. These neurons send their axons into the lateral funiculus to form the posterior spinocerebellar tract and are involved in processing proprioceptive information of the lower limbs. Within the ventral horn, a minority of large motor neurons (approximately 10 cells/section) were labeled, but to a much lesser extent.

Expression of Clone 10-29 receptor mRNA was also observed in substantia gelatinosa neurons of human fetal spinal cord and in dorsal root ganglia (DRG). Expression of Clone 10-29 in adult DRG remains to be confirmed. Standard hybridization controls with $^{35}$S-labeled sense probes were negative.

Preliminary studies using the human 10-29 probe on rat brain sections have yielded positive results. A weak, but specific, hybridization signal was detected over hippocampal CA pyramidal cells.

All references cited herein are fully incorporated herein by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A polynucleotide, except as existing in nature, consisting of nucleotides encoding a protein with the amino acid sequence of SEQ ID NO:1.

2. An expression vector comprising the polynucleotide of claim 1.

3. A host cell transformed with the vector of claim 2.

4. A polynucleotide, except as existing in nature, wherein said polynucleotide has the sequence of nucleotides 65–1309 of SEQ ID NO:2.

5. An expression vector comprising the polynucleotide of claim 4.

6. A host cell transformed with the vector of claim 5.

7. A polynucleotide, except as existing in nature, comprising a nucleotide sequence encoding a protein with the amino acid sequence of SEQ ID NO:1.

8. An expression vector comprising the polunucleotide of claim 7.

9. A host cell transformed with the vector of claim 8.

10. A polynucleotide, except as existing in nature, comprising the sequence of nucleotides 65–1309 of SEQ ID NO:2.

11. An expression vector comprising the polynucleotide of claim 10.

12. A host cell transformed with the vector of claim 11.

* * * * *

SEQUENCE LISTING

<160> NUMBER OF SEQ ID NOS: 9

<210> SEQ ID NO 1
<211> LENGTH: 415
<212> TYPE: PRT
<213> ORGANISM: Homo sapiens

<400> SEQUENCE: 1

Met Ser Gly Met Glu Lys Leu Gln Asn Ala Ser Trp Ile Tyr Gln Gln
1               5                   10                  15

Lys Leu Glu Asp Pro Phe Gln Lys His Leu Asn Ser Thr Glu Glu Tyr
            20                  25                  30

Leu Ala Phe Leu Cys Gly Pro Arg Arg Ser His Phe Phe Leu Pro Val
        35                  40                  45

Ser Val Val Tyr Val Pro Ile Phe Val Val Gly Val Ile Gly Asn Val
    50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Leu Val Leu Leu
                85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Leu Val

```
            260                 265                 270
Leu Val Leu Val Phe Ala Ile Cys Trp Ala Pro Phe His Ile Asp Arg
        275                 280                 285

Leu Phe Phe Ser Phe Val Glu Glu Trp Thr Glu Ser Leu Ala Ala Val
        290                 295                 300

Phe Asn Leu Val His Val Val Ser Gly Val Leu Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
            340                 345                 350

His Asp Pro Gln Leu Pro Pro Ala Gln Arg Asn Ile Phe Leu Thr Glu
            355                 360                 365

Cys His Ser Val Glu Leu Thr Glu Asp Ile Gly Pro Gln Phe Leu Cys
        370                 375                 380

Gln Ser Ser Val His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 2
<211> LENGTH: 1360
<212> TYPE: DNA
<213> ORGANISM: Homo sapiens

<400> SEQUENCE: 2 ttttttttcct ggctcagctt gaaacagagc ctcgtaccag gggaggctca ggccttggat      60
tttaatgtca gggatggaaa aacttcagaa tgcttcctgg atctaccagc agaaactaga     120
agatccattc cagaaacacc tgaacagcac cgaggagtat ctggccttcc tctgcggacc     180
tcggcgcagc cacttcttcc tcccgtgtc tgtggtgtat gtgccaattt ttgtggtggg     240
ggtcattggc aatgtcctgg tgtgcctggt gattctgcag caccaggcta tgaagacgcc     300
caccaactac tacctcttca gcctggcggt ctctgacctc ctggtcctgc tccttggaat     360 gccccctggag gtctatgaga gtgtggcgcaa ctacccttc ttgttcgggc cgtgggctg     420 ctacttcaag acggccctct tgagaccgt gtgcttcgcc tccatcctca gcatcaccac     480
cgtcagcgtg gagcgctacg tggccatcct acacccgttc gcgccaaac tgcagagcac     540 ccggcgccgg gccctcagga tcctcggcat cgtctgggc ttctccgtgc tcttctccct     600
gcccaacacc agcatccatg gcatcaagtt ccactacttc cccaatgggt ccctggtccc     660
aggttcggcc acctgtacgg tcatcaagcc catgtggatc tacaatttca tcatccaggt     720
cacctccttc ctattctacc tcctccccat gactgtcatc agtgtcctct actacctcat     780
ggcactcaga ctaaagaagg acaaatctct tgaggcagat gaagggaatg caaatattca     840 agaccctgc agaaaatcag tcaacaagat gctgcttgtc ttggtcttag tgtttgctat     900
ctgttgggcc ccgttccaca ttgaccgact cttcttcagc tttgtggagg agtggactga     960
atccctggct gctgtgttca acctcgtcca tgtggtgtca ggtgtcttat tctacctgag    1020
ctcagctgtc aaccccatta tctataacct actgtctcgc cgcttccagg cagcattcca    1080
gaatgtgatc tcttctttcc acaaacagtg gcactcccag catgacccac agttgccacc    1140
tgcccagcgg aacatcttcc tgacagaatg ccactctgtg gagctgaccg aagatatagg    1200
tccccaattc ctatgtcagt catccgtgca caactctcac ctcccaacag ccctctctag    1260
```

```
tgaacagatg tcaagaacaa actatcaaag cttccacttt aacaaaacct gaattctttc      1320
agagctgact ctcctctatg cctcaaaact tcacagagga                            1360
```

<210> SEQ ID NO 3
<211> LENGTH: 20
<212> TYPE: DNA
<213> ORGANISM: PCR primer
<220> FEATURE:
<221> NAME/KEY: modified_base
<222> LOCATION: (1)..(20)
<223> OTHER INFORMATION: N at positions 12 and 18 are inosine

<400> SEQUENCE: 3

```
aarmtsaara cngcyacnaa                                                  20
```

<210> SEQ ID NO 4
<211> LENGTH: 20
<212> TYPE: DNA
<213> ORGANISM: PCR primer
<220> FEATURE:
<221> NAME/KEY: modified_base
<222> LOCATION: (1)..(20)
<223> OTHER INFORMATION: N at positions 12 and 18 is inosine

<400> SEQUENCE: 4

```
ayrgcgayrt anckrtcnac                                                  20
```

<210> SEQ ID NO 5
<211> LENGTH: 20
<212> TYPE: DNA
<213> ORGANISM: PCR primer

<400> SEQUENCE: 5

```
tggtcctgct ccttggaatg                                                  20
```

<210> SEQ ID NO 6
<211> LENGTH: 20
<212> TYPE: DNA
<213> ORGANISM: PCR primer

<400> SEQUENCE: 6

```
gcgaagcaca cggtctcaaa                                                  20
```

<210> SEQ ID NO 7
<211> LENGTH: 23
<212> TYPE: DNA
<213> ORGANISM: PCR primer

<400> SEQUENCE: 7

```
ggggaagtag tggaacttga tgc                                              23
```

<210> SEQ ID NO 8
<211> LENGTH: 21
<212> TYPE: DNA
<213> ORGANISM: PCR primer

<400> SEQUENCE: 8

```
tcctctgtga agttttgagg c                                                21
```

<210> SEQ ID NO 9
<211> LENGTH: 19
<212> TYPE: DNA
<213> ORGANISM: PCR primer

-continued

```
<400> SEQUENCE: 9
atcgtctggg gcttctccg                                                    19
```